US009210566B2

(12) United States Patent
Ziemianska et al.

(10) Patent No.: US 9,210,566 B2
(45) Date of Patent: Dec. 8, 2015

(54) METHOD AND APPARATUS FOR AUTOMATICALLY ADJUSTING THE OPERATION OF NOTIFICATIONS BASED ON CHANGES IN PHYSICAL ACTIVITY LEVEL

(71) Applicant: Apple Inc., Cupertino, CA (US)

(72) Inventors: Natalia A. Ziemianska, Cupertino, CA (US); Devrim Varoglu, Santa Clara, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 13/744,547

(22) Filed: Jan. 18, 2013

(65) Prior Publication Data

US 2014/0206327 A1    Jul. 24, 2014

(51) Int. Cl.
  *H04M 3/00*   (2006.01)
  *H04W 8/22*   (2009.01)
  *G06F 3/01*   (2006.01)

(52) U.S. Cl.
  CPC .................. *H04W 8/22* (2013.01); *G06F 3/011* (2013.01); *G06F 3/014* (2013.01)

(58) Field of Classification Search
  CPC .......... H04W 8/22; H04W 8/24; H04W 8/245
  USPC ............. 455/418, 419, 420, 550.1, 567, 90.1, 455/90.2
  See application file for complete search history.

(56) References Cited

U.S. PATENT DOCUMENTS 6,605,038 B1 * 8/2003 Teller et al. .................... 600/300
7,130,664 B1   10/2006 Williams
8,299,902 B1   10/2012 Roka
8,306,514 B1   11/2012 Nunally
8,483,665 B2    7/2013 Kissinger et al.
8,614,431 B2   12/2013 Huppi et al.
9,049,572 B2    6/2015 Kissinger et al.
2002/0004672 A1  1/2002 Florio et al.

(Continued)

FOREIGN PATENT DOCUMENTS

WO    2012021507 A2    2/2012

OTHER PUBLICATIONS

Sam Costello: "Using Do Not Disturb on iPhone", Jun. 15, 2012, pp. 1-1, XP055108302, Retrieved from the Internet: URL:https://web.archive.org/web/20130116134723/http://ipod.about.com/od/phonefeatures/a/Using-Do-Not-Disturb-On-Iphone.htm [retrieved Mar. 17, 2014].

(Continued)

*Primary Examiner* — Temica M Beamer
(74) *Attorney, Agent, or Firm* — Kilpatrick Townsend & Stockton, LLP

(57) ABSTRACT

A processor-based personal electronic device (such as a smartphone) is programmed to automatically respond to data sent by various sensors from which the user's activity may be inferred. One or more of the sensors may be worn by the user and remote from the device. A wireless communication link may be used by the device to obtain remote sensor data. Data from on-board sensors in the device—such as motion sensors, location sensors, and the like—may also be used to deduce the user's current activity. In one embodiment, an extended period of inactivity triggers a reminder to the user to get up, stretch and move about. In other embodiments, transitions in a user's activity level may be used to trigger reminders and/or set the state of the device (such as a Do Not Disturb state wherein notifications and alarms are suppressed).

30 Claims, 7 Drawing Sheets

(56) References Cited

U.S. PATENT DOCUMENTS

| | | |
|---|---|---|
| 2004/0145493 A1 | 7/2004 | O'Connor et al. |
| 2005/0172311 A1 | 8/2005 | Hjelt et al. |
| 2007/0043687 A1 | 2/2007 | Bodart et al. |
| 2008/0165022 A1 | 7/2008 | Herz |
| 2008/0319279 A1 | 12/2008 | Ramsay et al. |
| 2009/0182560 A1 | 7/2009 | White |
| 2009/0186633 A1 | 7/2009 | Yonker et al. |
| 2011/0267196 A1 | 11/2011 | Hu et al. |
| 2012/0084248 A1 | 4/2012 | Gavrilescu |
| 2012/0158943 A1 | 6/2012 | Esteve Balducci et al. |
| 2014/0085077 A1 | 3/2014 | Luna et al. |
| 2014/0101611 A1 | 4/2014 | Lang et al. |
| 2014/0171132 A1 | 6/2014 | Ziemianska et al. |
| 2014/0171146 A1 | 6/2014 | Ma et al. |
| 2014/0172873 A1 | 6/2014 | Varoglu et al. |

OTHER PUBLICATIONS

Office Action mailed Jan. 27, 2015 in U.S. Appl. No. 13/715,096, 11 pages.

Non-Final Office Action mailed on Sep. 26, 2014 for U.S. Appl. No. 13/714,753, 30 pages.

Non-Final Office Action mailed on Mar. 27, 2014 for U.S. Appl. No. 13/714,753, 21 pages.

International Search Report and Written Opinion of the International Searching Authority mailed on Mar. 25, 2014 for PCT Patent Application No. PCT/US2014/010637, 10 pages.

"DPAC Dynamically Programmable Alarm Clock," Web Post and Video Demonstration based on an EE Capstone Competition Design Project presented at Northeastern University on Apr. 8, 2010, [online], [retrieved on Oct. 27, 2014], retrieved from the internet: <URL: http://egaertner.com/dpac>, 16 pages.

Pina, Laura, A., et al., "Fitbit+: A behavior-based intervention system to reduce sedentary behavior," CHI 2012, May 7-12, 2012, Austin, TX, USA, 4 pages.

Office Action mailed Apr. 27, 2015 in U.S. Appl. No. 13/714,753, 35 pages.

Final Office Action mailed Sep. 3, 2015 in U.S. Appl. No. 13/714,753, 37 pages.

Final Office Action mailed Sep. 9, 2015 in U.S. Appl. No. 13/715,096, 10 pages.

* cited by examiner

METHOD AND APPARATUS FOR AUTOMATICALLY ADJUSTING THE OPERATION OF NOTIFICATIONS BASED ON CHANGES IN PHYSICAL ACTIVITY LEVEL

BACKGROUND OF THE INVENTION

This invention relates to personal electronic devices. More particularly, it relates to the alarm and notification functions of smartphones.

A smartphone is a mobile phone built on a mobile operating system and having advanced computing capability and connectivity. The first smartphones combined the functions of a personal digital assistant (PDA) with a mobile phone. Later models added the functionality of portable media players, compact digital cameras, pocket video cameras, and GPS navigation units to form one multi-use device. Many current smartphones also include high-resolution touchscreens for input and web browsers that display standard web pages as well as mobile-optimized sites. High-speed data access may be provided by Wi-Fi and/or Mobile Broadband.

Wi-Fi is a widely-used technology that allows an electronic device to exchange data wirelessly (using radio waves) over a computer network, including high-speed Internet connections. The Wi-Fi Alliance defines Wi-Fi as any "wireless local area network (WLAN) products that are based on the Institute of Electrical and Electronics Engineers' (IEEE) 802.11 standards". However, since most modern WLANs are based on these standards, the term "Wi-Fi" is used in general English as a synonym for "WLAN".

A device that can use Wi-Fi (such as a personal computer, video-game console, smartphone, tablet, or digital audio player) can connect to a network resource such as the Internet via a wireless network access point. Such an access point (or "hotspot") typically has a range of about 65 feet (20 meters) indoors and a greater range outdoors. Hotspot coverage can comprise an area as small as a single room with walls that block radio waves or as large as many square miles—this may be achieved by using multiple overlapping access points.

Mobile broadband is the term used for wireless Internet access through a portable modem, mobile phone, USB wireless modem, or other mobile devices. A smartphone is basically a cellular telephone with built-in applications and Internet access. In addition to digital voice service, current smartphones provide text messaging, e-mail, Web browsing, and video playback and calling. In addition to their built-in functions, smartphones can run myriad free and paid applications, turning the cellphone into a mobile personal computer.

In addition to radio transmitters and receivers for interacting with cellular telecommunications systems, many smartphones have additional sensors that provide input to their various systems. For example, Apple Inc.'s iPhone® 5 smartphone includes at three-axis gyro, an accelerometer, a proximity sensor and an ambient light sensor.

The iPhone display may respond to a number of sensors. A proximity sensor deactivates the display and touchscreen when the device is brought near the face during a call. This is done to save battery power and to prevent inadvertent inputs from contact with the user's face and ears. An ambient light sensor adjusts the display brightness which in turn saves battery power. A 3-axis accelerometer senses the orientation of the phone and changes the screen accordingly, allowing the user to easily switch between portrait and landscape mode. Photo browsing, web browsing, and music playing support both upright and left or right widescreen orientations.

Certain smartphones have a "do not disturb" mode. When the "do not disturb" mode is activated (e.g., via a Settings menu), the phone suppresses most forms of communication—phone calls, text messages, alarms, social media notifications, and the like. When this mode is enabled, the phone will not light up or vibrate at all, so the user can get through a meeting or go to bed without being disturbed by the outside world. However, all of those notifications may get captured and appear in a "Notification Center" when the phone's display is turned on by the user.

The user may configure the "Do not disturb" feature to function on a predefined schedule, or may simply turn it on and off as needed. The user may also specify certain contacts—sometime designated as "VIPs"—who are allowed to get through to the user even if the phone is in "do not disturb" mode.

In certain implementations, when a call comes in, the user can choose to answer or ignore it, as usual, or may immediately reply with a text message. The user may also set the smartphone to remind him or her about the call later—either at a specific time, or when leaving the current location (as determined from the phone's location sensors).

Various options may allow the Do Not Disturb settings on a smartphone to be further customized. For example, an option for "Repeated Calls" may allow activation of a mode wherein whenever someone calls back a second time from the same number within a certain time interval, the second call will not be silenced.

BRIEF SUMMARY OF THE INVENTION

A processor-based personal electronic device (such as a smartphone) is programmed to automatically respond to data sent by various sensors from which the user's activity may be inferred. One or more of the sensors may be worn by the user and remote from the device. A wireless communication link may be used by the device to obtain remote sensor data. In certain embodiments, data from on-board sensors in the device—such as motion sensors, location sensors, ambient light sensors, and the like—may also be used to deduce the user's current activity. In yet other embodiments, user data (such as calendar entries) may also be used to determine likely user activity and adjust device notifications accordingly.

In one particular representative embodiment, the invention comprises a process for automatically generating a reminder to stand-up and stretch after 3 hours of sedentary activity. This may further be moderated by the time of day (e.g., don't generate a reminder if the user is asleep). Another example, based on a transition from active to idle, may be to set a reminder to call a certain person after the user completes his or her daily run. Yet another example, based on a transition from idle to running, may be to start a certain music playlist when the user begins to run.

BRIEF DESCRIPTION OF THE SEVERAL VIEWS OF THE DRAWING(S)

DETAILED DESCRIPTION OF THE INVENTION

Figure 1:
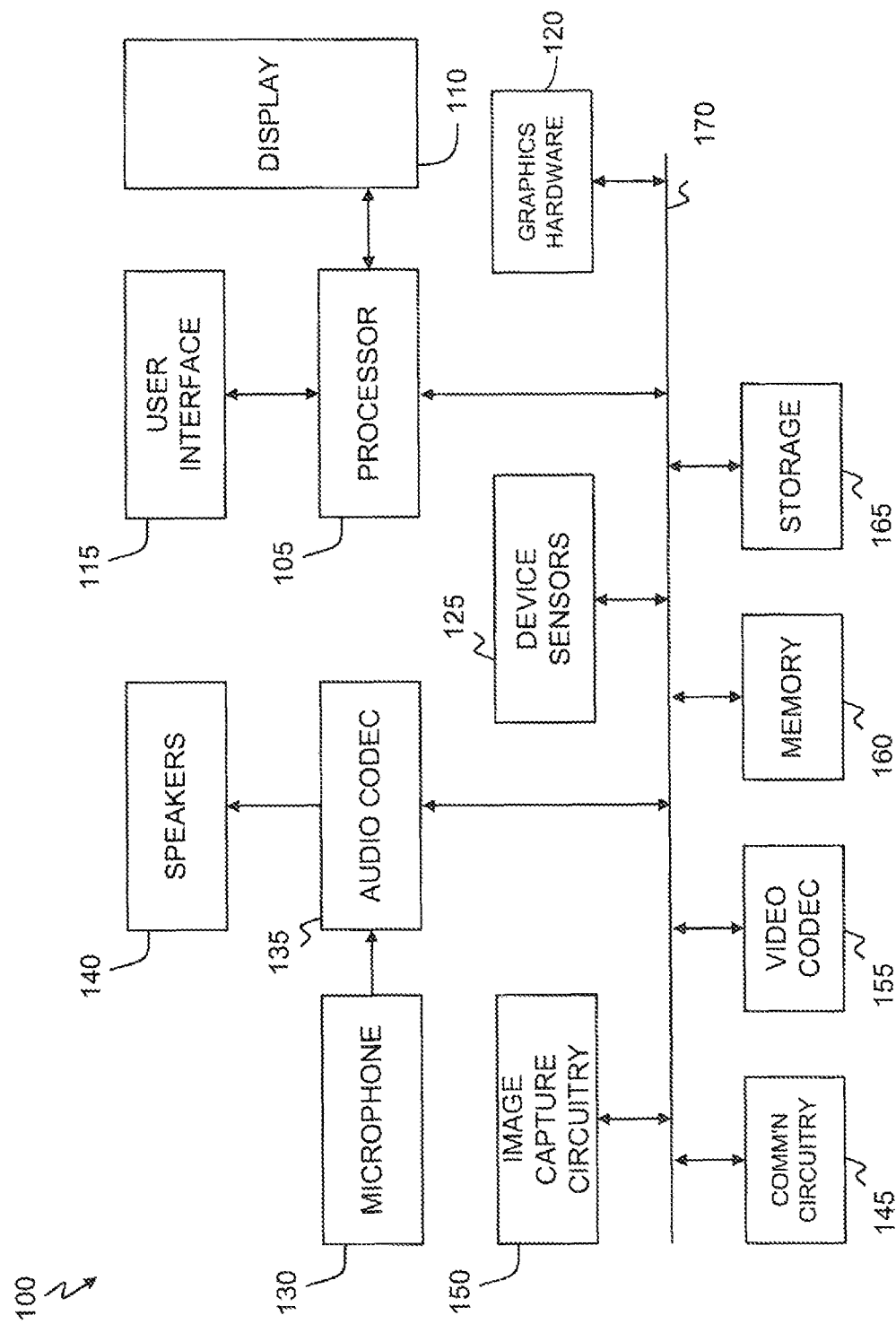
FIG. 1 is a block diagram of a processor-based device.

Referring to FIG. 1, a simplified functional block diagram of illustrative electronic device 100 is shown according to one embodiment. Electronic device 100 could, for example, be a smartphone, personal media device, portable camera, or a tablet, notebook or desktop computer system. As shown, electronic device 100 may include processor 105, display 110, user interface 115, graphics hardware 120, device sensors 125 (e.g., proximity sensor/ambient light sensor, accelerometer and/or gyroscope), microphone 130, audio codec(s) 135, speaker(s) 140, communications circuitry 145, image capture circuit or unit 150, video codec(s) 155, memory 160, storage 165, and communications bus 170.

Processor 105 may execute instructions necessary to carry out or control the operation of many functions performed by device 100 (e.g., such as the processing of data obtained from device sensors 125). Processor 105 may, for instance, drive display 110 and receive user input from user interface 115. User interface 115 can take a variety of forms, such as a button, keypad, dial, a click wheel, keyboard, display screen and/or a touch screen. Processor 105 may be a system-on-chip such as those found in mobile devices and include one or more dedicated graphics processing units (GPUs). Processor 105 may be based on reduced instruction-set computer (RISC) or complex instruction-set computer (CISC) architectures or any other suitable architecture and may include one or more processing cores. Graphics hardware 120 may be special purpose computational hardware for processing graphics and/or assisting processor 105 perform computational tasks. In one embodiment, graphics hardware 120 may include one or more programmable graphics processing units (GPUs).

Image capture circuitry 150 may capture still and video images that may be processed to generate images. Output from image capture circuitry 150 may be processed, at least in part, by video codec(s) 155 and/or processor 105 and/or graphics hardware 120, and/or a dedicated image processing unit incorporated within circuitry 150. Images so captured may be stored in memory 160 and/or storage 165. Memory Memory (EPROM), and Electrically Erasable Programmable Read-Only Memory (EEPROM). Memory 160 and storage 165 may be used to retain computer program instructions or code organized into one or more modules and written in any desired computer programming language. When executed by, for example, processor 105 such computer program code may implement one or more of the methods described herein. 160 may include one or more different types of media used by processor 105, graphics hardware 120, and image capture circuitry 150 to perform device functions. For example, memory 160 may include memory cache, read-only memory (ROM), and/or random access memory (RAM). Storage 165 may store media (e.g., audio, image and video files), computer program instructions or software, preference information, device profile information, and any other suitable data. Storage 165 may include one more non-transitory storage mediums including, for example, magnetic disks (fixed, floppy, and removable) and tape, optical media such as CD-ROMs and digital video disks (DVDs), and semiconductor memory devices such as Electrically Programmable Read-Only Memory.

An electronic device such as device 100 may receive inputs from on-board device sensors 125 which sensors may be of the types described, above—i.e., proximity sensors, accelerometers, gyroscopes, ambient light sensors and location sensors. In addition, it may receive signals and/or data from remote sensors via communication circuitry 145. Such remote sensors may be worn by the user of the device—e.g., wrist motion sensors, pulse rate sensors, breathing rate sensors, and the like. It will be appreciated by those skilled in the art that processor 105 of system 100 may be programmed to receive input data from the sensors and deduce from that data the current activity of the user. The activity of the user may be used to automatically select one or more states (or "settings") of the device.

By way of example, consider a case wherein device 100 is a smartphone. For an extended period of time beginning at about 11:00 p.m. on a weekday (the day and time being available to processor 105 from the clock and calendar features of the phone and/or a network to which the phone is connected), the built-in accelerometers and gyroscopes report no movement of the device and the ambient light sensor reports dim or dark conditions. Remote sensors worn by the user report infrequent arm movement and depressed pulse and breathing rates. No keyboard or touchscreen inputs are made. No calls or messages are sent. The phone may sense that it is connected to a charger. From all this information, a process running on processor 105 may reasonably infer that the user is asleep. The process may assign a probability to this inference based on certain preselected parameters of the data. The processor may use the calculated probability in deciding what, if any, actions to take based on the information.

The probability calculation may employ pattern recognition techniques. For example, if a certain determined user activity (e.g., sleeping) occurs repeatedly at about the same time in about the same place every day for about the same length of time, a higher probability (degree of confidence) may be assigned to that determination.

Various embodiments may best be understood by reference to the following examples and exemplary embodiment(s) illustrated in the drawing figures. Methods according to the invention allow a processor-based device such as a smartphone to dynamically set and/or reset reminders based on the activity level and/or activity transitions (of the user and/or the device).

EXAMPLE 1

Figure 2:
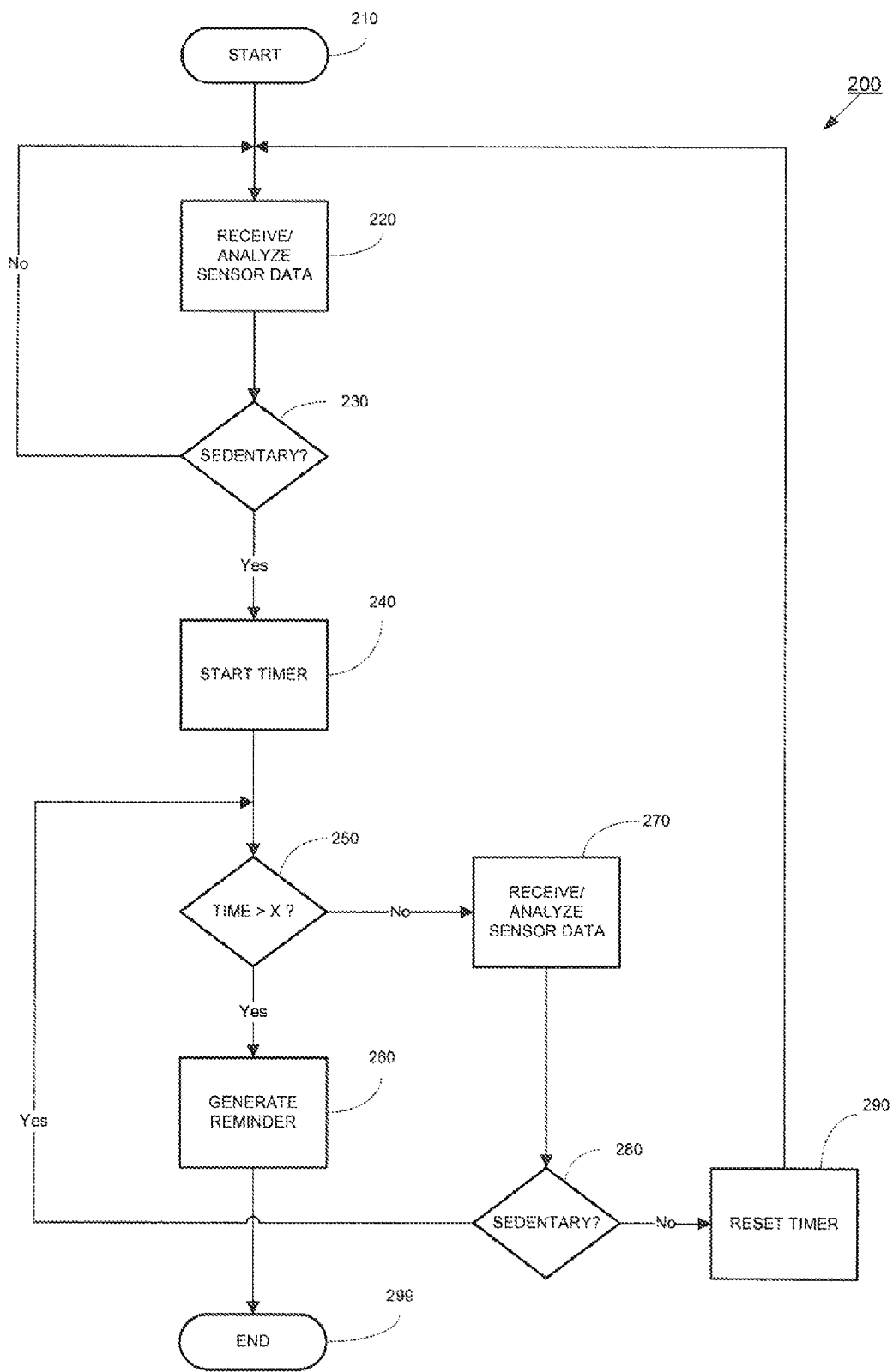
FIG. 2 is flowchart of a process according to a first representative embodiment of the invention.

Referring now to exemplary process 200 illustrated in flowchart form in FIG. 2, it may be seen how the invention may be used to remind a user to get up, stretch and move about if an extended period of inactivity is detected.

The process may begin at 210 with the user selecting the process to run in the background of his or her processor based device.

At 220, the device may receive and analyze data from various onboard and/or external sensors, as described above. At 230, the device may make a determination from the sensor data whether the user is sedentary (i.e., low activity level). For example, the device may determine from the motion sensors (accelerometers) and/or location sensors that the device is generally not moving and a remote pulse rate sensor may indicate a relatively low user heart rate. If it does not seem that the user is sedentary ("No" branch at 230), the device may continue to receive and analyze sensor data at 230 and continue to monitor for a sedentary state at 230.

If a sedentary state is detected ("Yes" branch at 230), the device may start a timer at 240 and then make another determination at 280 (from sensor data received and analyzed at 270) whether the user's sedentary state is continuing. If so ("Yes" branch at 280), the timer count may be checked to see if the sedentary state has persisted for a preselected minimum time X. If so ("Yes" branch at 250), the device may proceed to generate a reminder for the user at 260. For example, the device may sound a tone and display a message such as: "You have been sedentary for X [units of time]. You should get up, stretch and move about." The process is then terminated at 299. In certain embodiments, the process may monitor the subsequent activity level of the user to determine whether the advice was timely acted upon with the possible activation of subsequent reminders if increased activity.

If the user's sedentary state does not persist for the minimum preselected time X ("No" branches at 250 and 280) the timer may be reset at 290 and the system may return to receiving and analyzing sensor data at 220 and determining at 230 whether the user is in a sedentary state. In this way, the system may continually monitor the user's activity level and issue reminders if a sedentary period having a duration longer than the preselected time X is detected.

EXAMPLE 2

Figure 3:
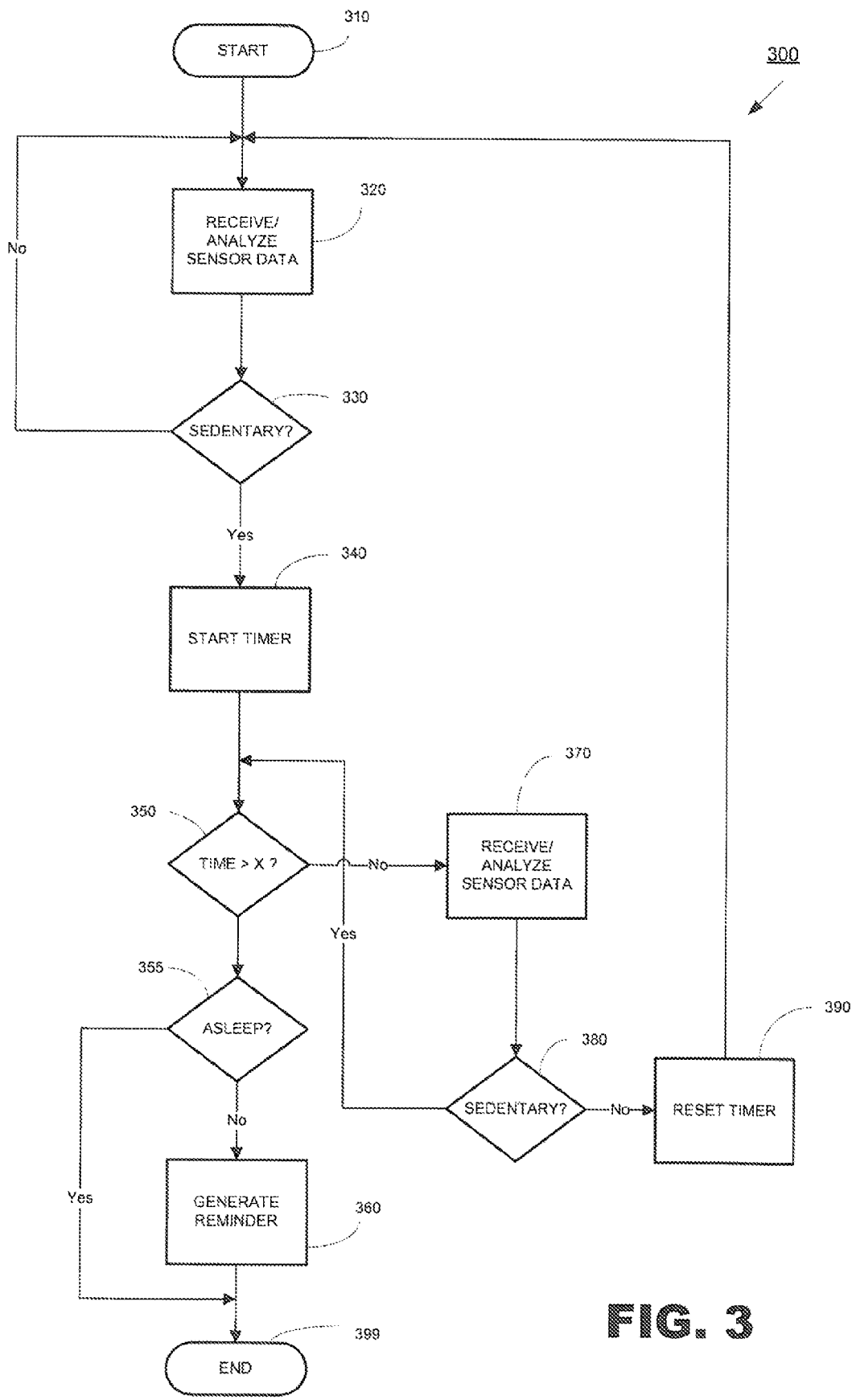
FIG. 3 is flowchart of a process according to a second representative embodiment of the invention.

This exemplary process (300 in FIG. 3) is a refinement of the process of Example 1 wherein reminders to get up, stretch and move about are suppressed if the user is likely asleep.

The process may begin at 310 with the user selecting the process to run in the background of his or her processor based device.

At 320, the device may receive and analyze data from various onboard and/or external sensors, as described above. At 330, the device may make a determination from the sensor data whether the user is sedentary (i.e., low activity level). For example, the device may determine from the motion sensors (accelerometers) and/or location sensors that the device is generally not moving and a remote pulse rate sensor may indicate a relatively low user heart rate. If it does not seem that the user is sedentary ("No" branch at 330), the device may continue to receive and analyze sensor data at 330 and continue to monitor for a sedentary state at 330.

If a sedentary state is detected ("Yes" branch at 330), the device may start a timer at 340 and then make another determination at 380 (from sensor data received and analyzed at 370) whether the user's sedentary state is continuing. If so ("Yes" branch at 380), the timer count may be checked to see if the sedentary state has persisted for a preselected minimum time X. If so ("Yes" branch at 350), the device may proceed to a determination at 355 of whether the user is likely asleep. In certain embodiments, this determination may include a consideration of the time of day (available from the internal clock of the device and/or network time data). For example, if the user is inactive from about 11:00 p.m. to about 6:00 a.m. on a weekday, it may be reasonable to infer that he or she is asleep. Whether the device is connected to a charger may also be a factor in the determination. In certain embodiments, the user's pattern of activity may be a factor in determining whether the user is likely asleep.

If it is determined that the user is likely asleep ("Yes" branch at 355) the process may skip the generation of a reminder at 360 and conclude at 399. If, one the other hand, the determination is that the user is not likely asleep ("No" branch at 355), the process may generate a reminder for the user at 360. For example, the device may sound a tone and display a message such as: "You have been sedentary for X [units of time]. You should get up, stretch and move about." The process is then terminated at 399. In certain embodiments, the process may monitor the subsequent activity level of the user to determine whether the advice was timely acted upon with the possible activation of subsequent reminders if increased activity.

If the user's sedentary state does not persist for the minimum preselected time X ("No" branches at 350 and 380) the timer may be reset at 390 and the system may return to receiving and analyzing sensor data at 320 and determining at 330 whether the user is in a sedentary state. In this way, the system may continually monitor the user's activity level and issue reminders if a sedentary period having a duration longer than the preselected time X is detected and it is unlikely the user is asleep.

EXAMPLE 3

Figure 4:
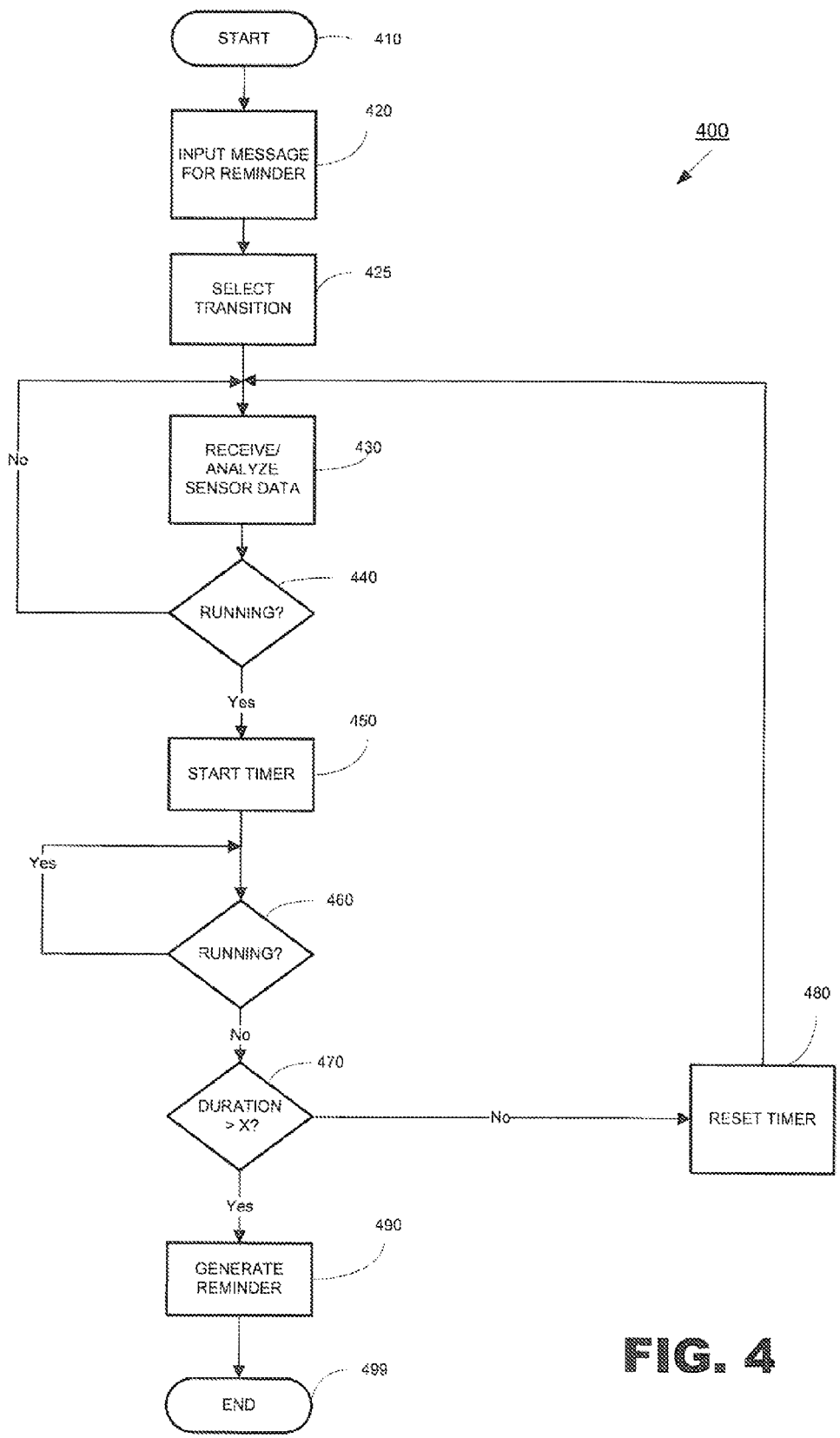
FIG. 4 is flowchart of a process according to a third representative embodiment of the invention.

An exemplary process according to the invention that employs an activity level transition to trigger a user-selected reminder is illustrated in flowchart form in FIG. 4 as process 400.

The process may begin at 410 with the user of a device selecting the particular function from a list of optional functions. At 420, the user may input a particular message for the reminder. As an example, the user may input "call Steve." In certain embodiments, the message may be selected from a list of messages which may include system generated messages and/or messages previously input by the user. At 425, the user is prompted to select a specific transition that will trigger the reminder. The selection may be from a list of selections presented by the system. For the purposes of the illustrated example, the selected transition is "when I have finished running."

At 430, the device may receive and analyze data from various onboard and/or external sensors, as described above. At 440, the device may make a determination from the sensor data whether the user is running. For example, the device may determine from the motion sensors (accelerometers) that there is a periodic, generally up-and-down motion and from location sensors that the device is moving over the ground at a speed consistent with a person running. A remote pulse rate sensor may indicate an elevated heart rate. If it does not seem that the user is running ("No" branch at 440), the device may continue to receive and analyze sensor data at 430 and continue to monitor for running at 440.

If running is detected ("Yes" branch at 440), the device may start a timer at 450 and continue to monitor for running activity at 460. If the running activity is continuing ("Yes" branch at 460), the process continues monitoring in a loop. However, when running ceases (no branch at 460), the timer count may be checked at 470 and if it does not exceed a preselected interval X (no branch at 470), the timer may be reset at 480 and the process returns to 430 for receiving and analyzing sensor data to determine (at 440) whether the user is running. In this way, a short burst of running is not mistaken by the system for an exercise-type run.

When an exercise run having a duration greater than preselected interval X comes to an end ("Yes" branch at 470), the system may generate a reminder at 490 and display the message input by the user at 420 before concluding at 499. In the illustrated case, a tone may sound and the message "call Steve" may be displayed on the screen of the device.

EXAMPLE 4

Figure 5:
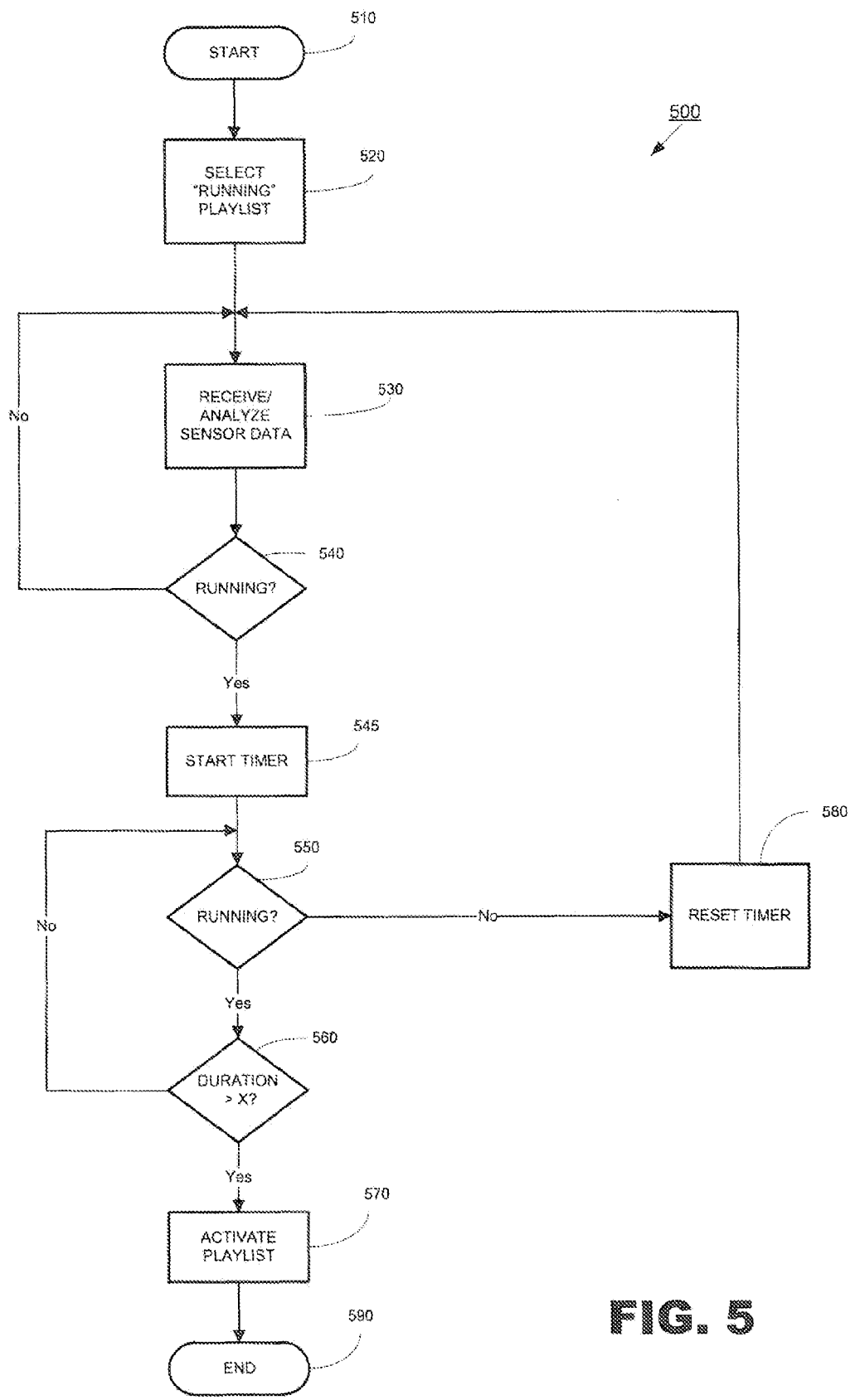
FIG. 5 is flowchart of a process according to a fourth representative embodiment of the invention.

A representative process 500 is illustrated in flowchart form in FIG. 5. In this particular embodiment, a user of a device selects a certain music playlist to listen to when he or she goes for a run. The device automatically detects the change in activity and activates the playlist.

The user may initiate the process at 510 by, for example, activating a setup menu on the device and enabling this particular function. The process may then present a list of stored playlists and, at 520, the user may select one of the stored playlists as his or her designated "running playlist."

At 530, the device may receive and analyze data from various onboard and/or external sensors, as described above. At 540, the device may make a determination from the sensor data whether the user is running. For example, the device may determine from location sensors that it is moving at a speed between about 6 and about 15 MPH and the data from the motion sensors (accelerometers) may indicate that the device is moving generally up and down in a rhythmic pattern from which the device may infer that the user is running. If it does not seem that the user is running ("No" branch at 540), the device may continue to receive and analyze sensor data at 530 and monitor for running activity at 540.

If running is detected ("Yes" branch at 540), the device may start a timer at 545 and then make another determination at 550 whether the running activity is continuing. If so ("Yes" branch at 550), the timer count may be checked to see if the running activity has continued for a preselected minimum time X. If so ("Yes" branch at 560), the device may proceed with activation of the selected "running" playlist at 570 and the process concludes at 590. If, however, the running does not continue for at least the preset duration ("No" branch at 550), the timer is reset at 580 and the process resumes receiving and analyzing sensor data at 530 and monitoring for running activity at 540. In this way, a short burst of running—e.g., running to catch a bus—is not mistaken for the beginning of an exercise run.

EXAMPLE 5

Figure 6A:
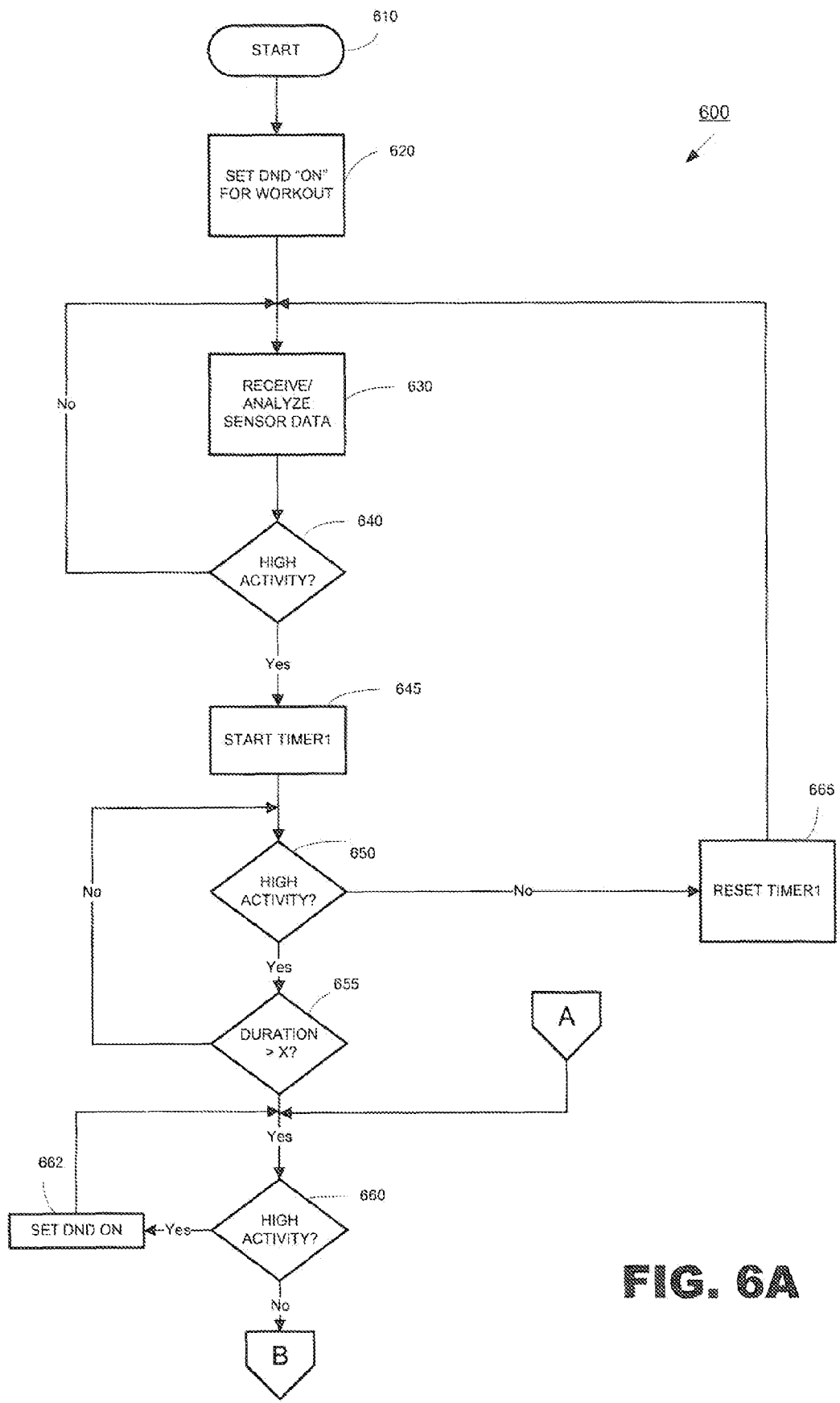
FIG. 6 is flowchart (in two parts, FIG. 6A and FIG. 6B) of a process according to a fifth representative embodiment of the invention.
Figure 6B:
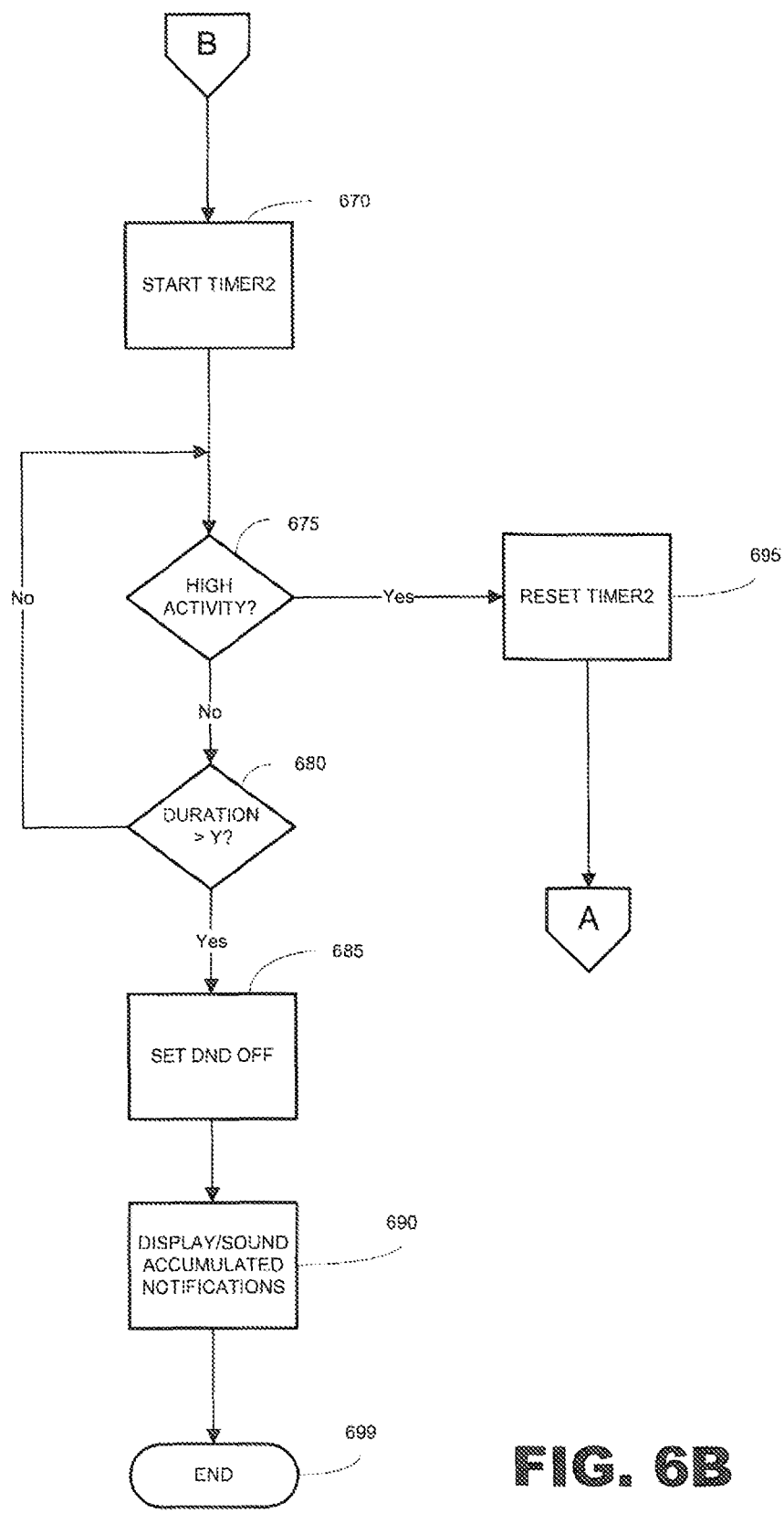

A representative process 600 is illustrated in flowchart form in FIGS. 6A and 6B. In this particular embodiment, a user of a device may opt for entering the Do Not Disturb state whenever he or she is performing an exercise workout. The device automatically detects the change in activity level and places the device in its Do Not Disturb state for the duration of the workout.

The user may initiate the process at 610 by, for example, activating a setup menu on the device and enabling this particular function.

At 630, the device may receive and analyze data from various onboard and/or external sensors, as described above. At 640, the device may make a determination from the sensor data whether the user is exercising (i.e., high activity level). For example, the device may determine from the motion sensors (accelerometers) that the device is moving at an increased rate (and perhaps in a generally rhythmic pattern) and a remote pulse rate sensor may indicate an elevated user heart rate. If it does not seem that the user is exercising ("No" branch at 640), the device may continue to receive and analyze sensor data at 630 and monitor for high activity at 640.

If exercise ("high activity") is detected ("Yes" branch at 640), the device may start a timer at 645 and then make another determination at 650 whether the high activity level is continuing. If so ("Yes" branch at 650), the timer count may be checked to see if the high activity level has continued for a preselected minimum time X. If so ("Yes" branches at 655 and 660), the device may proceed with activation of the Do Not Disturb state at 662 and the activity monitoring continues at 660. The process stays in this loop for the duration of the workout. If, however, the high activity does not continue for at least the preset duration ("No" branch at 650), the timer is reset at 665 and the process resumes receiving and analyzing sensor data at 630 and monitoring for high activity level at 640. In this way, a short burst of activity—e.g., running to catch a bus—is not mistaken for the beginning of an exercise workout.

When the high activity level ceases (no branch at 660) the process may start a second timer at 670 and continue to monitor activity level at 675. If a lower level of activity is sustained for more than a preselected interval Y ("Yes" branch at 680), the process may proceed to deactivate the Do Not Disturb function at 685 and, at 690, present the accumulated, suppressed notifications which occurred during the workout period. The process then concludes at 699. If, however, the lower activity state is not sustained for the preselected period Y ("Yes" branch at 675), Timer2 may be reset at 695 and the process may return to monitoring the user's activity level at 660. In this way, a brief period of lower activity level—e.g., a water break—is not mistaken for the end of a workout.

In yet another embodiment, the user may manually select the Do Not Disturb state at the beginning of a workout and the automatic process may deactivate the Do Not Disturb function at the conclusion of the workout.

EXAMPLE 6

In a process similar to those described above, the user may select a reminder to be displayed if a certain activity is not performed within a certain period of time. For example, the user may set a reminder to go for a run if he or she has not been for a run in the past X days (where X is a number input by the user). The system may then continually monitor for running-type activity (as determined from sensor data) and keep a running count of consecutive days in which no running-type activity was detected. If sustained running activity is detected, the counter resets. If, however, the count exceeds X days, a reminder is generated.

Although particular embodiments of the present invention have been shown and described, they are not intended to limit what this patent covers. One skilled in the art will understand that various changes and modifications may be made without departing from the scope of the present invention as literally and equivalently covered by the following claims.

What is claimed is:
1. A non-transitory program storage device comprising instructions stored thereon to cause one or more processors to:
   receive data from at least one sensor responsive to a user's physical activity level;
   determine, based on the received sensor data, that the user has initiated a workout; and
   change a notification state of a device based at least in part on determining that the user has initiated a workout, wherein the notification state determines whether the device generates a notification of an incoming communication.

2. A program storage device as recited in claim 1 wherein the at least one sensor is selected from the group consisting of motion sensors, pulse rate sensors, breathing rate sensors, orientation sensors, ambient light sensors, proximity sensors and location sensors.

3. A program storage device as recited in claim 1 wherein the at least one sensor comprises an apparatus selected from the group consisting of accelerometers, magnetometers, gyroscopes, photocells, charge coupled devices, global navigation satellite system receivers, Wi-Fi transceivers, cellular telephone transceivers and Assisted GPS receivers.

4. A program storage device as recited in claim 1 wherein the at least one sensor is a remote sensor worn by the user.

5. A program storage device as recited in claim 1 further comprising instructions to activate a preselected notification in response to determining that the user has initiated a workout.

6. A program storage device as recited in claim 1 wherein the notification state is changed to a do not disturb state.

7. A non-transitory program storage device as recited in claim 1 wherein the instructions further comprise instructions to:
suppress a notification to perform a certain activity if the activity is detected within a preselected time period.

8. A processor-based system comprising:
a processor;
at least one sensor responsive to the activity level of a user and in data communication with the processor; and,
a memory storing instructions for causing the processor to
receive data from at least one sensor responsive to a user's activity level;
determine, based on the received sensor data, that the user has initiated a workout; and,
change a notification state of a device based at least in part on determining that the user has initiated a workout, wherein the notification state determines whether the device generates a notification of an incoming communication.

9. A processor based system as recited in claim 8 wherein the at least one sensor is selected from the group consisting of motion sensors, pulse rate sensors, breathing rate sensors, orientation sensors, ambient light sensors, proximity sensors and location sensors.

10. A processor based system as recited in claim 8 wherein the at least one sensor comprises an apparatus selected from the group consisting of accelerometers, magnetometers, gyroscopes, photocells, charge coupled devices, global navigation satellite system receivers, Wi-Fi transceivers, cellular telephone transceivers and Assisted GPS receivers.

11. A processor based system as recited in claim 8 wherein the at least one sensor is a remote sensor worn by the user.

12. A processor based system as recited in claim 8 wherein the instructions further comprise instructions to activate a certain, preselected reminder in response to determining that the user has initiated a workout.

13. A processor based system as recited in claim 8 wherein the notification state is changed to a do not disturb state.

14. A processor based system as recited in claim 8 wherein the instructions further comprise instructions to suppress a notification to perform a certain activity if the activity is detected within a preselected time period.

15. A non-transitory program storage device comprising instructions stored thereon to cause one or more processors to:
receive data from at least one sensor responsive to a user's physical activity level;
determine, based on the received sensor data, that the user has initiated a workout; and,
activate a do not disturb function of a device based at least in part on determining that the user has initiated a workout.

16. A program storage device as recited in claim 15 further comprising instructions to activate a music playlist in response to determining that the user has initiated a workout.

17. A program storage device as recited in claim 16 wherein the change in physical activity level is a change to running activity.

18. A program storage device as recited in claim 17 wherein the running activity is determined at least in part by translational movement within a preselected range of speeds.

19. A program storage device as recited in claim 17 wherein the running activity is determined at least in part by periodic accelerations in a preselected direction.

20. A program storage device as recited in claim 15 further comprising activating a display of previously suppressed notifications after the workout ends.

21. A program storage device as recited in claim 15 further comprising instructions to measure the duration of a change in the user's activity level and activate the function only if the duration of the change exceeds a preselected period.

22. A program storage device as recited in claim 15 further comprising instructions to:
prompt a user to input a desired reminder to be displayed upon a preselected change in activity level.

23. A program storage device as recited in claim 1 wherein determining, based on the received sensor data, that the user has initiated a workout includes:
detecting a pattern of motion indicative of a workout activity; and
determining that the pattern of motion continues for at least a preset duration.

24. A program storage device as recited in claim 23 wherein the pattern of motion indicative of a workout activity includes a pattern of motion indicative of running.

25. A program storage device as recited in claim 24 wherein detecting the pattern of motion indicative of running includes detecting, based on location sensor data, that the device is moving at a speed consistent with running.

26. A program storage device as recited in claim 24 wherein detecting the pattern of motion indicative of running includes detecting, based on accelerometer data, that the device is moving in a rhythmic pattern consistent with running.

27. A program storage device as recited in claim 23 wherein detecting the pattern of motion indicative of a workout activity includes detecting, based on accelerometer data, that the device is moving at an increased rate.

28. A program storage device as recited in claim 23 wherein detecting the pattern of motion indicative of a workout activity includes detecting, based on pulse rate sensor data, that the user has an elevated heart rate.

29. A program storage device as recited in claim 1 wherein the incoming communication includes at least one of:
a phone call;
a text message;
an alarm; or
a social-media notification.

30. A processor based system as recited in claim 8 wherein the incoming communication includes at least one of:
a phone call;
a text message;
an alarm;
a social-media notification; or
a non-workout-related communication.

* * * * *